United States Patent [19]

Rolf et al.

[11] 4,177,667
[45] Dec. 11, 1979

[54] QUICK RESPONSE HUMIDITY CHAMBER

[75] Inventors: Steven R. Rolf, Sundance, Wyo.; James L. DeVries, Sioux Falls; T. Ashworth, Rapid City, both of S. Dak.

[73] Assignee: The United States of America as represented by the Secretary of the Navy, Washington, D.C.

[21] Appl. No.: 882,849

[22] Filed: Mar. 3, 1978

[51] Int. Cl.² ............................................. G01N 25/56
[52] U.S. Cl. ......................................................... 73/1 G
[58] Field of Search .................................. 73/1 G, 4 R

[56] References Cited
U.S. PATENT DOCUMENTS

| | | | |
|---|---|---|---|
| 3,273,376 | 9/1966 | Aronson | 73/4 R |
| 3,458,076 | 7/1969 | Babcock | 215/6 |
| 3,731,848 | 5/1973 | Nakanishi | 222/219 |

OTHER PUBLICATIONS

Instrument Practice, Dec. 1957, Humidity Step Function Generator, p. 1266.

Primary Examiner—S. Clement Swisher
Attorney, Agent, or Firm—R. S. Sciascia; Paul S. Collignon

[57] ABSTRACT

An apparatus and technique for changing the characteristics of a fluid medium in order to test static response of sensors within that medium. In particular, in testing the static response of a humidity sensor, a first sealed enclosure surrounds a humidity sensor and is retained within a second sealed enclosure. Both enclosures may be purged to have a predetermined relative humidity, one different from the other. The seal of the first chamber is then broken in such a manner that the fluid of the second enclosure subjects the sensor to a different relative humidity.

6 Claims, 1 Drawing Figure

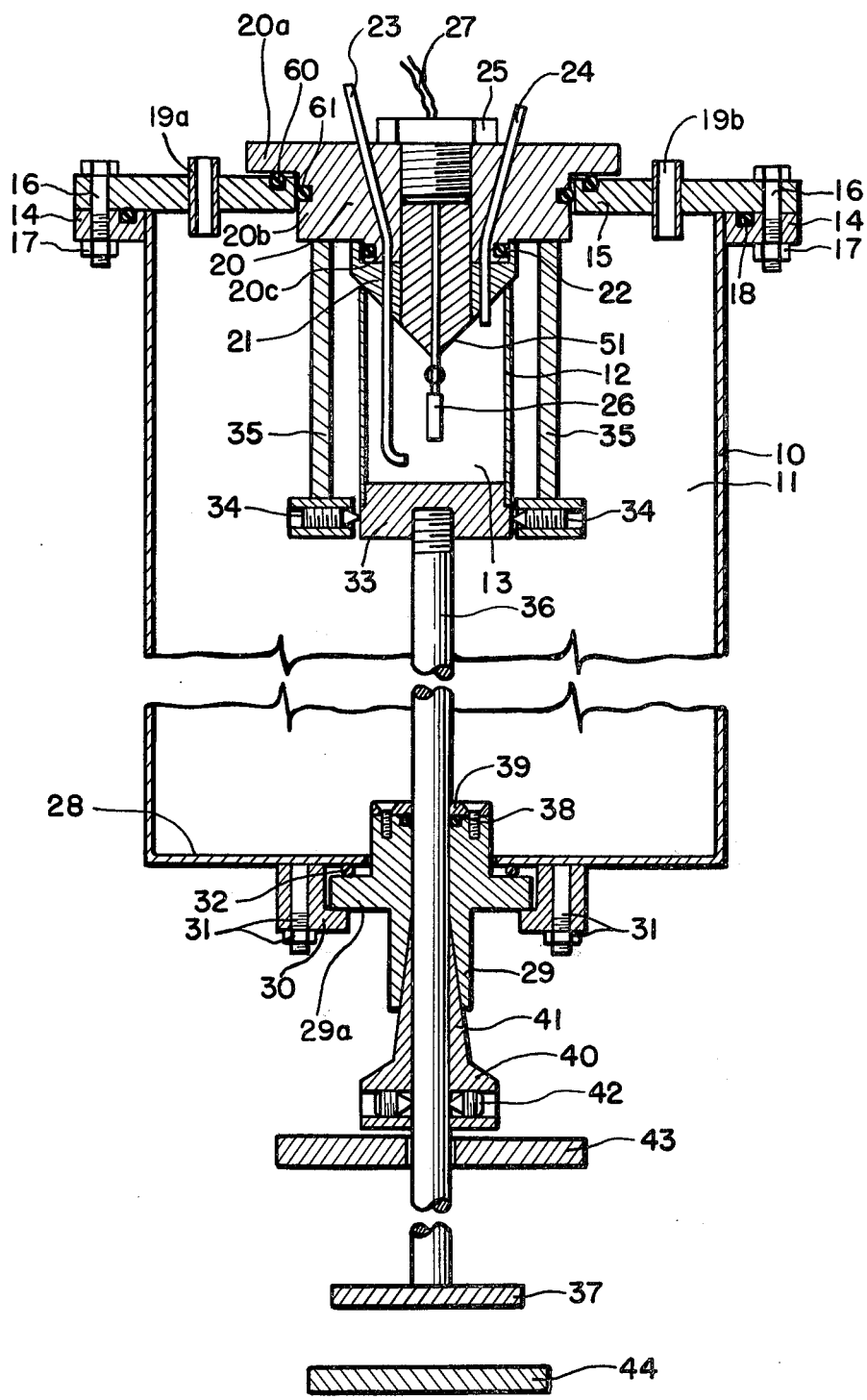

QUICK RESPONSE HUMIDITY CHAMBER

BACKGROUND OF THE INVENTION

The present invention relates to techniques for testing instrumentation response to changing fluid characteristics and more particularly to improved devices and techniques for providing changes in relative humidity to enable the observation of sensor response.

As rapid changes in technology lead to the development of more sophisticated instrumentation, knowledge of the operation and efficiency of such instrumentation under different environmental conditions is necessary to circumvent problems that may be created by those different environments. New techniques must therefore be developed which will simulate various environmental conditions to enable the calibration and observation of measuring instruments prior to practical use. In the areas of humidity testing particularly, it is often desirable to ascertain the response of humidity sensors to rapid changes in relative humidity. While prior systems have been able to change the humidity of the environment surrounding such sensors, the same has been accomplished by observing the dynamic response only (i.e., the response obtained by observing sensor action in a flowing stream of gas). Since such systems are not capable of rapidly changing the relative humidity without deleterious effects due to desorption and adsorption caused by flow mechanisms, sensor response to anticipated environmental effects cannot be observed. There is, therefore, a continuing need for systems capable of providing test simulations for instrumentation of this type.

Accordingly, the present invention has been developed to overcome the specific shortcomings of the above-known and similar techniques and to provide a system for rapidly changing the relative humidity of the fluid medium surrounding a test sensor.

SUMMARY OF THE INVENTION

It is therefore an object of the present invention to provide a technique for rapidly changing the characteristics of a fluid volume.

Another object of the invention is to provide a technique for testing the static response of a sensor to changes in the characteristics of fluid volumes.

Still another object of the invention is to provide an apparatus and technique for measuring the static response of a humidity sensor exposed to rapid changes in relative humidity.

Yet another object of the invention is to provide for rapid equilibriation of two volumes of gas having different relative humidities.

In order to accomplish the above and other objects, the present invention employs a first enclosure which includes a humidity sensor positioned therein. Inlet and outlet passages are provided to purge the first enclosure to establish a first predetermined relative humidity. The first enclosure is surrounded by and sealed from a second enclosure having a predetermined volume ratio relative to the first enclosure and inlet and outlet passages for adjusting the relative humidity of the second enclosure at a value independent of the humidity in the first enclosure. A shaft attached to said first enclosure and extending through said second enclosure is actuated to cause movement of the first enclosure such that the seal between the two enclosures is removed. As the fluid flow equalizes between both enclosures, the sensor response to changes in relative humidity can be easily observed.

Other objects, advantages and novel features of the invention will become apparent from the following detailed description when taken with the accompanying drawing wherein:

BRIEF DESCRIPTION OF THE DRAWING

The FIGURE is a schematic diagram illustrating the testing system according to the present invention.

BRIEF DESCRIPTION OF A PREFERRED EMBODIMENT

Referring now to the FIGURE, the device for changing the magnitude of the relative humidity in an enclosed volume is shown to include an outer enclosure 10 defining a volume 11 and an inner enclosure 12 defining a volume 13. The outer enclosure may typically be formed as a cylindrical metal casing having an opening at one end surrounded by a circular flange 14. Circular plate 15 is positioned across the opening in the casing 10 and retained thereon by a nut and bolt combination 16 and 17 extending through plate 15 and flange 14. A seal 18, such as a conventional O-ring, is provided between the surfaces of the plate 15 and flange 14 in order to hermetically seal the connection between those elements. Inlet and outlet tubes 19a and 19b are provided in the plate 15 to allow for the introduction and withdrawal of gas when connected to a vacuum source or any other apparatus as may be required to establish a particular relative humidity within the volume 11.

The plate 15 is constructed to include a circular opening having a center axis concentric with the longitudinal axis through the center of the cylinder 10. An annular member 20 is removably positioned within the opening in plate 15 and includes a flange portion 20a abutting the outside of plate 15 and a shoulder portion 20b extending through the noted opening. A hermetic seal is provided between the members 15 and 20 by O-rings 60 and 61, positioned as illustrated. The annular member 20 also includes a shoulder portion 20c projecting from shoulder 20b and having an annular conical member 21 attached thereto. A hermetic seal between members 20 and 21 is then provided by O-ring 22. Inlet and outlet tubes 23 and 24 extend through annular members 20 and 21 to provide passages for the introduction and withdrawal of gas to the volume 13 in a manner similar to volume 11. Mounting assembly 25 additionally extends through the circular opening in the annular member 20 and conical member 21 and has a configuration such that the surface formed by the members 21 and 25 within the volume 13 is the surface of a cone 51. Mounting assembly 25 additionally includes a sensor 26 attached thereto which extends to a position within the volume 13. Leads 27 are electrically attached to the sensor 26 and extend from the assembly 25 to enable connection of the sensor to external recording or measuring apparatus (not shown).

The opposite end of casing 10 is closed by an integral wall 28 having a circular opening therein. The circular opening has a center axis which is colinear with the center axis of the circular opening in annular member 20. A second annular member 29 is retained within the opening in wall 28 so that the center axis of the opening in the member 20 is also colinear with the axis of the opening in member 29. Member 29 is retained within the opening in wall 28 by a flange ring 30 which abuts against the shoulder 29a. The flange ring is retained by a stud and nut assembly 31 projecting from the wall 28 and extending through ring 30. An O-ring 32 positioned between the wall 28 and shoulder 29a provides a hermetic seal between those elements.

The inner enclosure 12 is formed as a cylindrical metal casing having an opening at one end thereof and closed at the opposite end by a cap 33. The longitudinal axis through the center of the cylindrical casing 12 is positioned so that it is colinear with the axis of each opening through members 20 and 29. This positioning is provided by set screws 34 which project from vertically extending members 35. The members 35 are in turn rigidly attached to the surface of shoulder 20b and serve as a guide for the movement of the casing 12 along its longitudinal axis. Set screws 34 may be formed from teflon or nylon and are positioned to cooperate with opposed longitudinal grooves on the surface of the member 12 to provide slidable contact or movement of the member 12 along the identified axis. A shaft 36 is threadably attached to the cap 33 and extends through the opening in the annular member 29 before terminating in a strike plate 37. The space between the surface of the shaft 36 and the member 29 is hermetically sealed by an O-ring 38 which is retained by ring 39 attached to member 29. An annular collar 40 having a tapered surface 41 surrounds the shaft 36 and is adjustably retained thereon by set screws 42, radially extending through one end of collar 40. The collar 40 is thus positioned on the shaft 36 such that the tapered surface 41 forcibly abuts against a corresponding tapered surface in the annular member 29 when the open end of casing 12 is in contact with the surface 51. The end of the cylinder 12 is so constructed as to contact the surface 51 and provide a seal therewith when held in engagement by frictional contact of the tapered surface 41. Actuator mass 43 is additionally located around the shaft 36 and allowed to freely move along such shaft between member 40 and strike plate 37. The bumper pad 44 is retained at a fixed distance from the striking plate 37 such that following movement of the shaft 36 through a predetermined distance, the bumper pad 44 will prevent further movement of the shaft 36.

The operation of the system will now be described with reference to the noted FIGURE. Under normal circumstances, the system operates to effect a change in fluid equilibrium between the two volumes 11 and 13 enclosed by members 10 and 12. In the present example, it is desired to establish the response of the sensor 26 to a rapid change in the value of a physical characteristic of the fluid volume, in this case the relative humidity. Initially, therefore, each volume is provided with a specific quantity of gas through its respective inlet and outlet tubes 19a, 19b, 23, and 24, to establish two fluid volumes, each having a different value of relative humidity. The static condition is fixed by terminating the dynamic flow of fluid through the tubes when equilibrium at the desired humidity has been achieved for both volumes. Thereafter, with the sensor 26 mounted within the inner volume 13, and the appropriate relative humidities established, the relative humidity of the inner volume is changed by breaking the seal between the end of the inner chamber 12 and the conical surface of 21 and 51. To accomplish this, the mass 43 is dropped through a distance along a length of the shaft 36 by the force of gravity until it comes into contact with the plate 37. The collision of mass 43 and plate 37 produces a force which overcomes the frictional engagement of the tapered surfaces at 41 and causes the shaft 36 to move in the direction of mass 43 until the plate 37 strikes the bumper pad 44. Movement of the shaft 36 thus causes the end of enclosure 12 to move away from the surface formed by element 21 for a distance equal to the distance traveled by the plate 37. Following release of the seal between the conical surface and enclosure 12, the low pressure region created at the base of volume 13 by virtue of the motion of enclosure 12 draws fluid from the outer enclosure 10. The movement of the enclosure 12 is such as to cause fluid from the enclosure 10 to flow over the sensor (and thus subject it to a different relative humidity) prior to mixing and fluid equalization between the enclosures. The fluid from enclosure 10 is guided over sensor 26 by the conical surface formed by elements 21 and 25 which acts to increase the speed of fluid equalization by avoiding oscillations that might normally be created by dead space above the volume 13. The rapid exchange of fluid in the two volumes changes the relative humidity detected by the sensor 26 and thereby enables the static response of the sensor to be measured. The conical configuration formed by the surfaces of elements 21 and 51 causes the fluid originally within enclosure 12 to remain in that enclosure, thereby precluding mixing of the fluid from enclosures 12 and 10 immediately following actuation.

As can be seen, the ratio of the volumes of the two enclosures can be varied to effect any concentration of respective fluids as may be desired. By way of example, the two enclosures can be made to have a volume ratio of 100:1 and can be fixed to change the relative humidity by 1% when the outer volume is initially 0% relative humidity and the inner volume is 100% relative humidity. By using a vacuum to dynamically establish the equilibrium of the relative humidity in both volumes, pressure can be established to simulate higher altitudes wherein knowledge of the response of such sensors is particularly important. While the establishment of very low humidities may require extended dynamic flow under vacuum conditions in order to allow all adsorbed moisture to evaporate, the final volumes will be an accurate reflection of the established relative humidity.

Using the above apparatus and technique, the static response of any sensor to a particular parameter fixed by a fluid medium can be easily observed. The system provides a method of rapidly changing such parameters as humidity in time periods of about 0.1 seconds and allows the changes to be made in either direction, e.g., lower to higher relative humidity or vice versa. At the same time, the relative volumes enclosed by the two casings can be adjusted by altering the size of the two casings thereby enabling almost any percentage change and any absolute magnitude of relative humidity to be obtained in testing the static response. As noted, the initial condition can be achieved by a dynamic flow of gas through the fluid inlets and outlets; the flow is then terminated and the system operated in the static mode. Alternatively, the flow may be continued allowing the same system to be used for testing the dynamic responses of the same sensor. However, as a static system, the apparatus provides a fast response since it has freedom from the desorption effects normally found in dynamic systems.

While the invention has been described with particular reference to the assembly shown in the FIGURE, the same is only exemplary of the construction that may be used to establish the required fluid exchange. By way of example, the separation of the casings could be achieved through any known hydraulically actuated mechanism or other known mechanical arrangement. While the present structure allows for easy removal, replacement or adjustment of elements, the specific configurations of the enclosures and other elements could be altered to provide for simplified sealing and mounting in any desirable form suitable for the environment in which such testing will be performed. The surface of the casings could additionally be highly polished and gold plated to reduce moisture adsorption and desorption which might otherwise interfere with the accurate establishment of humidity conditions. In the described embodiment, the device requires that the conical surface 21 be of a material of some flexibility in order that an adequate seal be accomplished between 12 and 21. However, the system may be operated using differing initial pressures in enclosures 10 and 12 by removing component 21 and using O-ring 22 to form a hermetic seal between 12 and 20c.

Obviously many other modifications and variations of the present invention are possible in light of the above teachings. It is therefore to be understood that within the scope of the appended claims, the invention may be practiced otherwise than as specifically described.

What is claimed and desired to be secured by Letters Patent of the United States is:

1. A system for testing the response of sensors to fluid characteristics comprising,
    a first enclosure for retaining a first volume of fluid having a predetermined physical characteristic at a fixed value, said first enclosure having a circular opening at one end,
    means positioned within said first enclosure for measuring the value of said characteristic,
    a second enclosure for retaining a second volume of fluid having the same physical characteristic as said first volume but fixed at a different value, said first enclosure being positioned within said second enclosure,
    a conical surface projecting within said circular opening of said first enclosure to seal said first enclosure within said second enclosure, and
    means for causing the exchange of fluid between said volumes so that said means for measuring is subjected to the characteristic value of said second volume to provide a measurement of that value prior to fluid equilibration.

2. The system of claim 1 wherein said means for causing the exchange of fluid comprises means for moving said first enclosure away from said conical surface so as to break the seal therebetween, and wherein said conical surface is constructed to divert fluid from said second enclosure into the volume vacated by the fluid and said first enclosure and across said means for measuring in order to prevent fluid oscillation and immediate mixing between the two enclosures.

3. The system of claim 1 wherein said means for causing the exchange of fluid comprises,
    a shaft rigidly coupled to one end of said first enclosure and extending through a portion of said second enclosure,
    means for slidably supporting said first enclosure within said second enclosure, and
    means for applying a force to said shaft external to said second enclosure in order to cause said first enclosure to move away from said conical surface and break the seal therebetween.

4. The system of claim 3 wherein said means for applying a force comprises,
    a mass slidably retained along said shaft, and
    a plate rigidly attached to one end of said shaft, said mass being positioned to fall by the force of gravity against said plate to cause movement of the shaft and corresponding movement of the first enclosure away from said conical surface.

5. The system of claim 3 further including:
    a first annular collar attached to said second enclosure and slidably receiving said shaft; and
    a second annular collar adjustably attached to said shaft, said first and second annular collars having tapered surfaces designed to provide mating frictional engagement, said second collar being positioned on said shaft such that the frictional engagement between said collars will position said first enclosure in sealing engagement with said conical surface.

6. A technique for testing the response of sensors to fluid characteristics comprising,
    forming a first volume of fluid having a first value of relative humidity,
    positioning a sensor within said first volume of fluid for measuring the value of relative humidity,
    forming a second volume of fluid having a second value of relative humidity different from said first value of relative humidity, and
    causing the exchange of fluid between said volumes so as to subject said sensor to the relative humidity value of said second volume prior to fluid equilibration.

* * * * *